United States Patent
Park et al.

(10) Patent No.: US 10,667,757 B2
(45) Date of Patent: Jun. 2, 2020

(54) FEATURE EXTRACTION APPARATUS AND METHOD FOR BIOMETRIC INFORMATION DETECTION, BIOMETRIC INFORMATION DETECTION APPARATUS, AND WEARABLE DEVICE

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Young Soo Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 604 days.

(21) Appl. No.: 15/413,940

(22) Filed: Jan. 24, 2017

(65) Prior Publication Data

US 2018/0078215 A1   Mar. 22, 2018

(30) Foreign Application Priority Data

Sep. 20, 2016   (KR) .................. 10-2016-0120201

(51) Int. Cl.
*A61B 5/00* (2006.01)
*A61B 5/021* (2006.01)
*A61B 5/02* (2006.01)

(52) U.S. Cl.
CPC ............ *A61B 5/7278* (2013.01); *A61B 5/021* (2013.01); *A61B 5/02007* (2013.01); *A61B 5/02116* (2013.01); *A61B 5/681* (2013.01); *A61B 5/7235* (2013.01); *A61B 5/7239* (2013.01); *A61B 5/7246* (2013.01); *A61B 5/0002* (2013.01)

(58) Field of Classification Search
None
See application file for complete search history.

(56) References Cited

U.S. PATENT DOCUMENTS

| | | | |
|---|---|---|---|
| 6,954,700 B2 | 10/2005 | Higashida et al. | |
| 8,116,857 B2 | 2/2012 | Kimura et al. | |
| 9,275,013 B2 | 3/2016 | Baechler et al. | |
| 9,427,157 B2 | 8/2016 | Kang et al. | |
| 2004/0102710 A1 | 5/2004 | Kim | |

(Continued)

FOREIGN PATENT DOCUMENTS

| | | | |
|---|---|---|---|
| JP | 2009-11540 A | 1/2009 | |
| JP | 4792584 B2 | 10/2011 | |

(Continued)

OTHER PUBLICATIONS

Communication issued by the European Patent Office dated Oct. 17, 2017 in counterpart European Patent Application No. 17163719.2.

(Continued)

*Primary Examiner* — Sujoy K Kundu
*Assistant Examiner* — Terence E Stifter, Jr.
(74) *Attorney, Agent, or Firm* — Sughrue Mion, PLLC

(57) ABSTRACT

A feature extraction apparatus configured to perform biometric information detection includes a bio-signal obtainer configured to acquire a bio-signal; and a processor configured to decompose a waveform of the acquired bio-signal into component pulses and extract a feature for the biometric information detection based on characteristic points of the component pulses.

30 Claims, 22 Drawing Sheets

(56) References Cited

U.S. PATENT DOCUMENTS

| | | | |
|---|---|---|---|
| 2007/0016085 A1 | 1/2007 | Inukai et al. | |
| 2011/0201951 A1 | 8/2011 | Zhang | |
| 2012/0197140 A1* | 8/2012 | Okuda | A61B 5/02007 |
| | | | 600/500 |
| 2012/0232417 A1 | 9/2012 | Zhang | |
| 2013/0041271 A1* | 2/2013 | Ben-Ari | A61B 5/024 |
| | | | 600/506 |
| 2014/0249438 A1 | 9/2014 | Morikawa et al. | |
| 2015/0220486 A1 | 8/2015 | Karakonstantis et al. | |
| 2016/0242700 A1* | 8/2016 | Ferber | A61B 5/7278 |
| 2016/0270668 A1 | 9/2016 | Gil | |
| 2016/0331234 A1 | 11/2016 | Kang et al. | |

FOREIGN PATENT DOCUMENTS

| | | |
|---|---|---|
| KR | 10-0399737 B1 | 9/2003 |
| KR | 10-0955716 B1 | 5/2010 |
| KR | 10-0967994 B1 | 7/2010 |
| KR | 10-2013-0094103 A | 8/2013 |
| KR | 10-2014-0060737 A | 5/2014 |
| KR | 10-1503604 B1 | 3/2015 |
| KR | 10-2016-0043417 A | 4/2016 |

OTHER PUBLICATIONS

Yoon, et al., "Nonconstrained Blood Pressure Measurement by Photoplethysmography", Journal of the Optical Society of Korea, vol. 10, Issue No. 2, Jun. 2006, pp. 91-95.

Millasseau, et al., "The Vascular Impact of Aging and Vasoactive Drugs: Comparison of Two Digital Volume Pulse Measurements", American Journal of Hypertension, Ltd., vol. 16, Issue No. 6, Jun. 2003, pp. 467-472.

Baruch, et al., "Validation of the pulse decomposition analysis algorithm using central arterial blood pressure", BioMedical Engineering OnLine, vol. 13, Issue No. 96, 2014, pp. 1-19, http://www.biomedical-engineering-online.com/content/13/1/96.

Communication dated Jun. 8, 2018 issued by the European Patent Office in counterpart European Patent Application No. 17163719.2.

Xiaochuan He et al., "Secondary Peak Detection of PPG Signal for Continuous Cuffless Arterial Blood Pressure Measurement", IEEE Transactions on Instrumentation and Measurement, Jun. 1, 2014, pp. 1431-1439 (total 10 pages), vol. 63, No. 6, DOI: 10.1109/TIM.2014.2299524, XP011547677.

Mirko De Melis et al., "Blood pressure waveform analysis by means of wavelet transform", Medical & Biological Engineering & Computing, Sep. 30, 2008, pp. 165-173 (total 10 pages), vol. 47, No. 2, DOI: 10.1007/s11517-008-0397-9, XP019835301.

* cited by examiner

ASYMMETRIC

FEATURE EXTRACTION APPARATUS AND METHOD FOR BIOMETRIC INFORMATION DETECTION, BIOMETRIC INFORMATION DETECTION APPARATUS, AND WEARABLE DEVICE

CROSS-REFERENCE TO RELATED APPLICATION(S)

This application claims priority under 35 U.S.C. § 119(a) from Korean Patent Application No. 10-2016-0120201, filed on Sep. 20, 2016, in the Korean Intellectual Property Office, the disclosure of which is incorporated herein by reference in its entirety for all purposes.

BACKGROUND

Field

Methods and apparatuses consistent with exemplary embodiments disclosed herein relate to a technology for non-invasively detecting biometric information by extracting a feature from a bio-signal and using the extracted feature.

Description of Related Art

Due to the recent aging population, the increase in medical expenses, and the shortage of specialized medical service personnel, the research on IT-medical convergence technologies, in which the IT technologies and medical technologies are combined, is ongoing. In particular, monitoring of the health status of a human body is not limited only to being performed at a fixed place, such as a hospital, but is extended to a mobile healthcare field which provides monitoring of a user's health status at any place, such as at home and the office, at any time in daily life. Electrocardiography (ECG), photoplethysmogram (PPG), and Electromyography (EMG) signals are typical examples of a bio-signal that indicates the individual's health condition, and various bio-signal sensors for measuring such signals in daily life have been developed. In particular, in the case of a PPG sensor, a blood pressure of a user can be measured by analyzing a shape of a pulse wave which indicates the cardiovascular state of the user, etc.

PPG bio-signal research has shown that the full PPG signal is composed of a superposition of a propagation wave starting from the heart toward the body distal end and a reflection wave coming back from the body distal end. In addition, it is known that information used to estimate blood pressure can be obtained by extracting various features related to the propagation wave or the reflection wave.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided a feature extraction apparatus configured to perform biometric information detection, the feature extraction apparatus including: a bio-signal obtainer configured to acquire a bio-signal; and a processor configured to decompose a waveform of the acquired bio-signal into component pulses and extract a feature for the biometric information detection based on characteristic points of the component pulses.

The processor may include a waveform decomposer configured to obtain a subsequent component pulse based on a new bio-signal generated based on one of the component pulses.

The waveform decomposer may include: a pulse estimator configured to estimate a given component pulse to be decomposed, among the component pulses, based on the waveform of the bio-signal and thereby generate an estimation result; and a pulse generator configured to generate the given component pulse based on the estimation result.

The waveform decomposer may further include a pulse eliminator configured to, when the given component pulse is generated, eliminate the generated component pulse from the bio-signal, and when a number of generated component pulses is smaller than a pre-set number, estimate another subsequent component pulse based on another new bio-signal generated by eliminating the generated component pulse.

The pulse estimator may be configured to model a component pulse waveform function based on the waveform of the acquired bio-signal and estimate parameters of the component pulse waveform function.

The pulse estimator may be configured to model the component pulse waveform function to be bilaterally asymmetric with respect to a time axis, based on a Gaussian waveform function and an asymmetry factor.

The waveform decomposer may further include a factor adjuster configured to, when the given component pulse is estimated based on a current bio-signal and the asymmetry factor, adjust the asymmetry factor based on a new bio-signal generated by eliminating the estimated component pulse from the current bio-signal, and the pulse estimator may be configured to re-estimate the given component pulse based on the current bio-signal and the adjusted asymmetry factor.

The factor adjuster may be configured to adjust the asymmetry factor based on a determination that a mean time period of the eliminated component pulse is smaller than a time period at a peak point.

The processor may include a feature extractor configured to extract the feature for the biometric information detection based on characteristic points which include one or more of time, an amplitude, a standard deviation, and an offset of the decomposed component pulses.

The bio-signal obtainer may be configured to acquire the bio-signal by emitting light onto a user's skin and detecting light returning from the user's skin.

The feature extraction apparatus may further include a communicator configured to receive the bio-signal from a biometric information detection apparatus, forward the bio-signal to the bio-signal obtainer and transmit a result of processing based on the received bio-signal to the biometric information detection apparatus.

According to an aspect of another exemplary embodiment, there is provided a feature extraction method for biometric information detection, the feature extraction method including: acquiring a bio-signal; decomposing a waveform of the acquired bio-signal into component pulses; and extracting a feature for the biometric information detection based on characteristic points of each of the component pulses.

The decomposing may include obtaining a subsequent component pulse based on a new bio-signal generated based on one of the component pulses.

The decomposing may include: estimating a given component pulse to be decomposed, among the component pulses, based on the waveform of the bio-signal; and generating the given component pulse based on the estimation result.

The feature extraction method may further include, when the given component pulse is generated, eliminating the generated component pulse from the bio-signal, wherein the estimating of the given component pulse may include, when a number of generated component pulses is smaller than a pre-set number, estimating another subsequent component pulse based on another new bio-signal generated by eliminating the generated component pulse.

The estimating of the given component pulse may include modeling a component pulse waveform function based on the waveform of the bio-signal and estimating parameters of the component pulse waveform function.

The modeling of the component pulse waveform function may include modeling the component pulse waveform function to be bilaterally asymmetric with respect to a time axis, based on a Gaussian waveform function and an asymmetry factor.

The feature extraction method may further include adjusting the asymmetry factor for a waveform of the given component pulse to be estimated.

The adjusting of the asymmetry factor may include: estimating the given component pulse based on the bio-signal and the asymmetry factor; eliminating the estimated component pulse from the bio-signal; comparing a mean time period of the bio-signal from which the component pulse is eliminated with a time period at a peak point, and, in response to determining that the mean time period is smaller than the time period at a peak point, adjusting the asymmetry factor and re-estimating the given component pulse.

According to an aspect of another exemplary embodiment, there is provided a biometric information detection apparatus including: a measurer configured to emit light onto a user's skin, detect the light reflecting from the user's skin, and measure a bio-signal based on the detected light; and a processor configured to decompose a waveform of the bio-signal into component pulses, extract a feature of the bio-signal based on characteristic points of the component pulses, and detect biometric information based on the feature.

The processor may be further configured to obtain a subsequent component pulse based on a new bio-signal generated based on one of the component pulses.

The processor may be further configured to model a component pulse waveform function which is asymmetric with respect to a time axis, based on a Gaussian waveform function and an asymmetry factor, and decompose the bio-signal into the component pulses based on the modeled component pulse waveform function.

The processor may be further configured to extract the feature based on characteristic points which include one or more of time, an amplitude, a standard deviation, and an offset of the component pulses.

The biometric information detection apparatus may further include a communicator configured to transmit the measured bio-signal to a feature extraction apparatus and receive, from the feature extraction apparatus, at least one of one or more additional component pulses decomposed based on the bio-signal, characteristic points of each of the additional component pulses, and a feature extracted based on the characteristic points.

The biometric information may include one or more of blood pressure, a vascular age, a degree of arterial stiffness, an aortic pressure waveform, a stress index, and a degree of fatigue.

According to an aspect of another exemplary embodiment, there is provided a wearable device including: a main body; a measurer provided in the main body and configured to emit light onto a user's skin, detect the light reflecting from the user's skin, and measure a bio-signal based on the detected light; a processor provided in the main body and configured to acquire the bio-signal by controlling the measurer, decompose a waveform of the acquired bio-signal into component pulses, extract a feature based on characteristic points of the component pulses, detect biometric information using the extracted feature, and generate a processing result based on the detected biometric information; and a display provided in the main body and configured to display the processing result of the processor.

The display may include a first section configured to display the detected biometric information or changes in the detected biometric information.

The display may further include a second section configured to display component pulses used to detect biometric information which is selected from the first section.

The display may be configured to display a mark in the first section for indicating the detected biometric information or the biometric information selected from the first section.

The wearable device may further include a communicator provided in the main body and configured to establish a connection with an external device for communication and transmit the processing result of the processor to the external device via the connection.

Other features and aspects will be apparent from the following detailed description, the drawings, and the claims.

Figure 1:
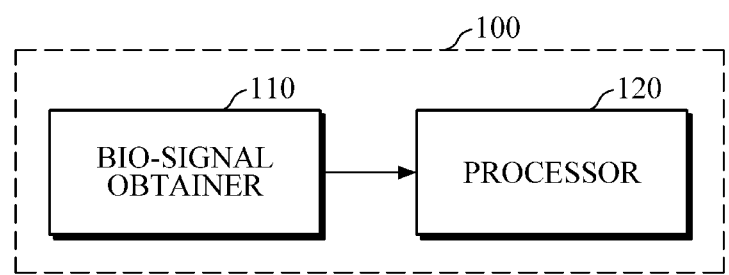
FIG. 1 is a block diagram illustrating a feature extraction apparatus according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Advantages and features of the technical disclosure and methods of achieving the same will be apparent by referring to the exemplary embodiments described below in detail with reference to the accompanying drawings. However, the scope of the disclosure is not limited to the exemplary embodiments described below and various modifications may be made thereto. The exemplary embodiments are merely provided to thoroughly disclose the exemplary embodiments and to convey the exemplary embodiments to one of ordinary skill in the art. The same reference numerals denote the same elements throughout the specification.

It will be understood that, although the terms first, second, etc., may be used herein to describe various elements, these elements should not be limited by these terms. These terms are only used to distinguish one element from another. As used herein, the singular forms "a", "an" and "the" are intended to include the plural forms as well, unless the context clearly indicates otherwise. Further, it will be understood that the terms "comprises" and/or "comprising" or "includes" and/or "including" specify the presence of stated elements, but do not preclude the presence or addition of one or more other elements. Terms such as " . . . unit" and "module" denote units that process at least one function or operation, and they may be implemented by using hardware, software, or a combination of hardware and software.

Hereinafter, exemplary embodiments of a feature extraction apparatus and method for detecting biometric information, a biometric information detection apparatus and a wearable device will be described in detail with reference to the accompanying drawings.

FIG. 1 is a block diagram illustrating a feature extraction apparatus according to an exemplary embodiment. The feature extraction apparatus 100 may be implemented in the form of a software or hardware module mounted in a terminal, such as a wearable device, a smartphone, a tablet PC, a desktop PC, a notebook PC, and the like, and a device for detecting biometric information, such as blood pressure. In addition, the feature extraction apparatus 100 may be implemented as an independent hardware device, and may be utilized for the purpose of research for analysis of a waveform of a bio-signal which is composed of the sum of a plurality of component pulses in this case. However, aspects of the exemplary embodiments are not limited to the above description, and various modifications may be made to the feature extraction apparatus 100 according to the purpose of utilization of the exemplary embodiments.

Referring to FIG. 1, the feature extraction apparatus 100 includes a bio-signal obtainer 110 and a processor 120. The bio-signal obtainer 110 and the processor 120 may be implemented by one or more circuits, processors, memories, or a combination thereof.

The bio-signal obtainer 110 may acquire a bio-signal of a subject for detecting biometric information and forward the acquired bio-signal to the processor 120. In this case, the biometric information may include blood pressure, a vascular age, a degree of arterial stiffness, an aortic pressure waveform, a stress index, a degree of fatigue, and the like. However, the biometric information is not limited to the above examples. In addition, the bio-signal for detecting the biometric information may be an electrocardiography (ECG) signal, a photoplethysmography (PPG) signal, an electromyography (EMG) signal, or the like.

Hereinafter, the exemplary embodiments will be described by focusing on an example of detection of blood pressure using a PPG signal (hereinafter, referred to as a "pulse wave signal"). However, this is only for the purpose of convenience of description, and the aspects of the exemplary embodiments are not limited thereto.

The bio-signal obtainer 110 may include a sensor to emit light onto the subject and detect light returning from the subject. In this case, the bio-signal obtainer 110 may drive the sensor in response to a predetermined control signal and acquire a pulse wave signal of the subject. In this case, the control signal may be generated by a control module implemented in the feature extraction apparatus 100. The control module may be implemented as one function of the processor 120 and may generate the control signal on the basis of a user's input. The sensor may drive a light source to emit light onto the subject in response to the control signal and may detect the light scattered or reflected from the subject to measure the pulse wave signal. In this case, the sensor may be mounted in the feature extraction apparatus 100, but is not limited thereto, and may be implemented as a separate hardware device.

When the bio-signal obtainer 110 acquires the bio-signal, the bio-signal obtainer 110 may perform pre-processing on the bio-signal, such as filtering, amplification of the bio-signal, or conversion into a digital signal.

The processor 120 may receive the bio-signal from the bio-signal obtainer 110 and analyze a waveform of the received bio-signal to extract a feature for detecting biometric information. For example, the processor 120 may obtain one or more component pulses decomposed on the basis of a full waveform of the received bio-signal. In this case, the number of component pulses to be decomposed on the basis of a bio-signal may be pre-set according to the type of biometric information to be detected. In addition, characteristic points, such as time, amplitude, and the like, may be acquired from each of the decomposed component pulses, and a combination of one or more characteristic points may be extracted as a feature for biometric information detection. In this case, the characteristic points extracted from each component pulse are not limited to the above description, and the characteristic points may include a variety of information according to a type of biometric signal, a characteristic of waveform, a type of biometric information to be detected, and the like.

Figure 2:
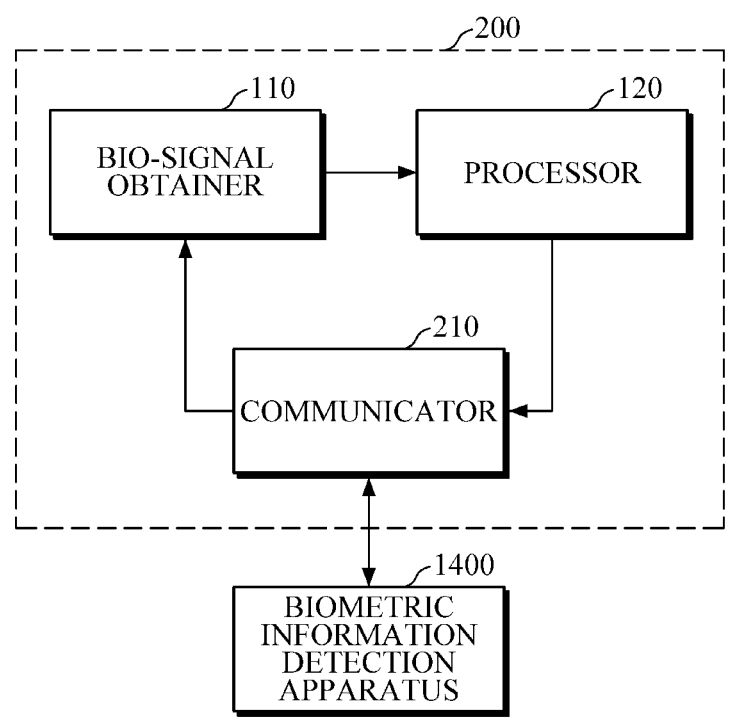
FIG. 2 is a block diagram illustrating a feature extraction apparatus according to another exemplary embodiment.

FIG. 2 is a block diagram illustrating a feature extraction apparatus according to another exemplary embodiment.

Referring to FIG. 2, the feature extraction apparatus 200 includes a bio-signal obtainer 110, a processor 120, and a communicator 210. According to the exemplary embodiment, the bio-signal obtainer 110 and the processor 120 may be implemented as one module by one or more circuits, memories, processors, or a combination thereof.

According to an exemplary embodiment, the bio-signal obtainer 110 may acquire a bio-signal from an external device which measures the bio-signal. For example, when the bio-signal obtainer 110 receives a bio-signal measurement control signal, the bio-signal obtainer 110 may control the communicator 210 to be connected to a biometric information detection apparatus 1400.

According to one example, the communicator 210 may access a communication network and be connected to the biometric information detection apparatus 1400 using a communication technology under the control of the bio-signal obtainer 110 and may receive biometric information from the biometric information detection apparatus 1400. In this case, the biometric information detection apparatus 1400 may include a sensor to measure a bio-signal, which will be described below, and may transmit the bio-signal measured from the subject to the communicator 210.

In this case, the communication technology may include, but is not limited to including, Bluetooth, Bluetooth Low Energy (BLE), Near-Field Communication (NFC), WLAN, ZigBee, Infrared Data Association (IrDA), Wi-Fi Direct (WFD), Ultra-Wideband (UWB), Ant+, Wi-Fi, and a mobile communication technology.

According to another example, in response to a connection request signal received from the biometric information detection apparatus 1400, the communicator 210 may be connected to the biometric information detection apparatus 1400 and receive a request for information used to detect biometric information and extraction of features used to detect biometric information using the bio-signal. In addition, the communicator 210 may transmit a processing result, which includes feature information using the bio-signal and is generated by the processor 120, to the biometric information detection apparatus 1400.

When the communicator 210 receives the bio-signal from the biometric information detection apparatus 1400, the communicator 210 may transmit the received bio-signal to the bio-signal obtainer 110. In this case, when the bio-signal obtainer 110 receives the bio-signal from the biometric information detection apparatus 1400, the bio-signal obtainer 110 may preprocess the received bio-signal and transmit the pre-processed signal to the processor 120.

The processor 120 may decompose the received bio-signal into one or more component pulses by analyzing the waveform of the received bio-signal and extract features used to detect biometric information by acquiring a characteristic point of each component pulse.

Hereinafter, various exemplary embodiments of the processors 120 of the feature extraction apparatuses 100 and 200, which are illustrated in FIGS. 1 and 2, respectively, will be described with reference to FIGS. 3 to 8.

Figure 3:
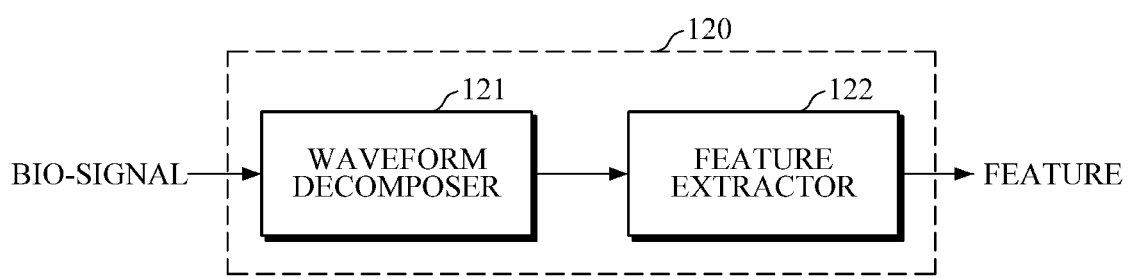
FIG. 3 is a block diagram illustrating an exemplary embodiment of a configuration of a processor of the feature extraction apparatus.
Figure 4A:
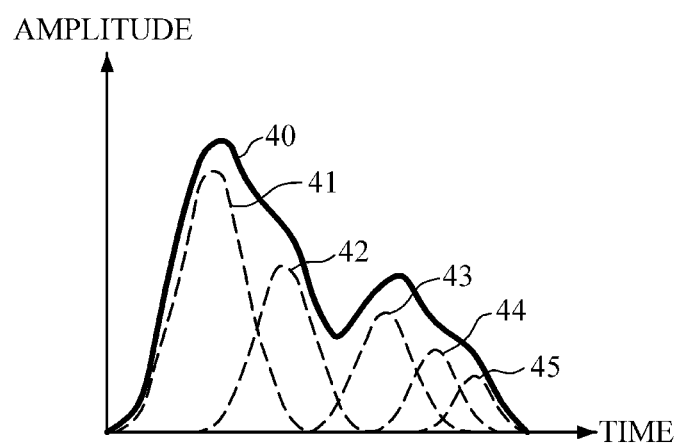
FIGS. 4A and 4B are diagrams for describing a general method of extracting a feature of a bio-signal.
Figure 4B:
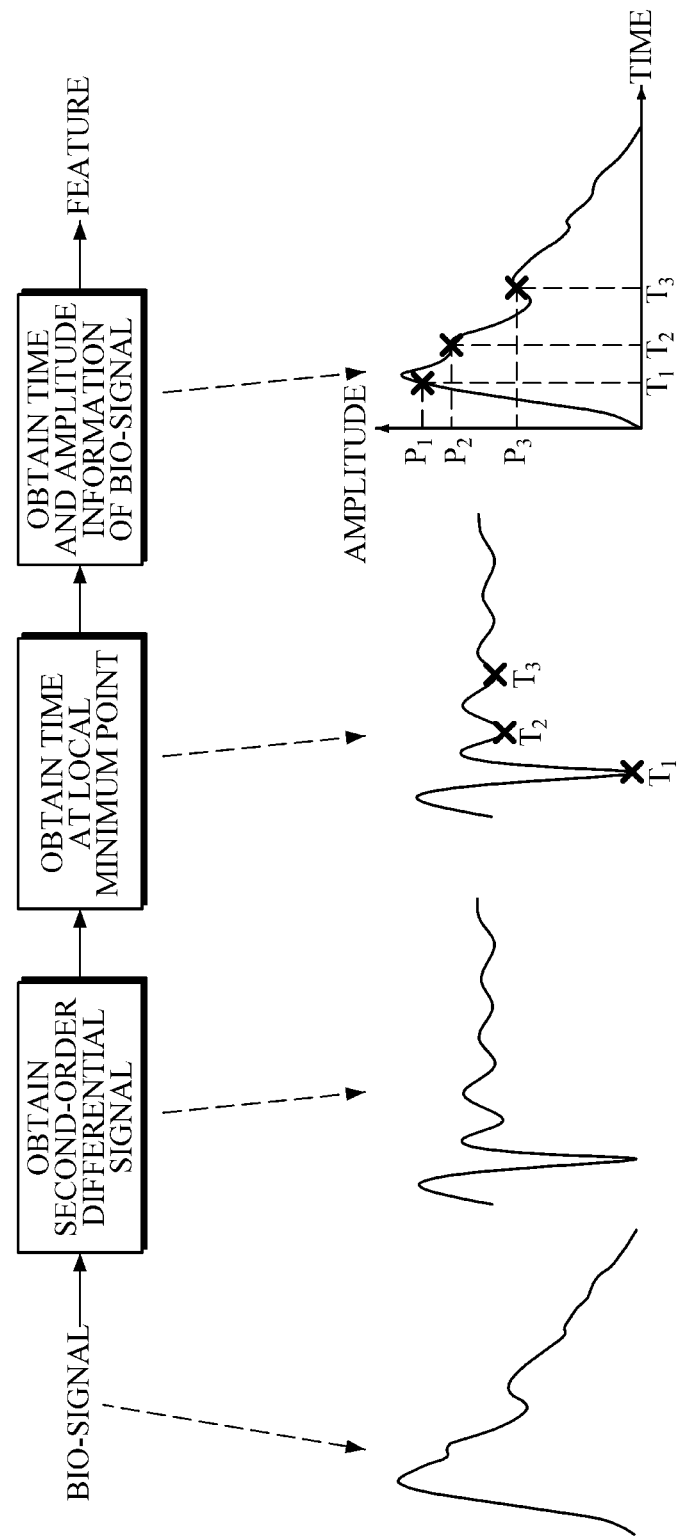

FIG. 3 is a block diagram illustrating an exemplary embodiment of a configuration of the processors 120 in the feature extraction apparatus 100 and 200. FIGS. 4A and 4B are diagrams for describing a general method of extracting a feature of a bio-signal.

Referring to FIG. 3, the processors 120 of the feature extraction apparatuses 100 and 200, which are illustrated in FIGS. 1 and 2, respectively, each include a waveform decomposer 121 and a feature extractor 122.

When the waveform decomposer 121 receives a bio-signal, the waveform decomposer 121 may decompose the received bio-signal into component pulses by analyzing a full waveform of the received bio-signal. In this case, the number of component pulses to be decomposed on the basis of a bio-signal may be pre-set according to various criteria, such as a type of biometric information, a characteristic of waveform, and the like. In addition, the waveform decomposer 121 may sequentially obtain a component pulse through decomposition based on the full waveform of the bio-signal. In this case, the component pulse decomposed from the bio-signal may be applied to the bio-signal for the decomposition of a subsequent component pulse. That is, as will be described below, after the first component pulse is decomposed on the basis of the full waveform of the bio-signal received from the bio-signal obtainer 110, a subsequent component pulse may be decomposed on the basis of the bio-signal to which the previously decomposed component pulse is sequentially applied.

For example, FIG. 4A illustrates a pulse wave signal 40 for measuring blood pressure and five component pulses 41, 42, 43, 44, and 45 that constitute the pulse wave signal 40. Generally, the pulse wave signal is composed of a superposition of a propagation wave starting from the heart toward the body distal end and a reflection wave coming back from the body distal end. A feature with a high correlation with the blood pressure may be extracted when time or amplitude information of each component pulse is appropriately combined. In general, since the first three component pulses are mainly used to estimate a blood pressure, the number of component pulses to be decomposed on the basis of a bio-signal may be set to "3". Subsequent pulses may not be observed in some persons, and may be difficult to find due to noise, or even when they are found, the subsequent pulses may be generally less correlated with blood pressure estimation.

FIG. 4B is a diagram for describing general procedures for extracting a feature using a bio-signal. A general apparatus for extracting a feature from a bio-signal may search for a local minimum point from a second-order differential signal of a bio-signal and may acquire time points $T_1$, $T_2$, and $T_3$ which correspond to the local minimum points and amplitudes P1, P2, and P3 of a full bio-signal that correspond to the time points $T_1$, $T_2$, and $T_3$ as characteristic points. In addition, features for detecting biometric information may be extracted using the acquired characteristic points. In this case, the local minimum point refers to a specific point in a part of the bio-signal observed where the decreasing signal increases again, and may also be referred to as a downward convex point.

As such, in the general method of extracting a feature, not a characteristic point of each component pulse, but amplitude information of the full waveform of the bio-signal is used as a characteristic point to detect a feature, so that there is a limitation in accurately detecting biometric information.

Referring back to FIG. 3, the feature extractor 122 may acquire a characteristic point from each component pulse which is decomposed from the full waveform of the bio-signal by the waveform decomposer 121, and the feature extractor 122 may extract a feature using the acquired information. In this case, the characteristic point may include time, amplitude and standard deviation which are acquired from each component point, and amplitude information of the full waveform of the bio-signal which corresponds to the time of each component pulse, but is not limited thereto.

For example, when the waveform composer 121 decomposes the pulse wave signal 40 shown in FIG. 4A into three component pulses 41, 42, and 43, the feature extractor 122 may acquire amplitude information A1, A2, and A3 from the respective component pulses 41, 42, and 43 and extract a feature F for blood pressure estimation by combining the amplitude information A1, A2, and A3 of the respective component pulses 41, 42, and 43 using Equation 1 below.

$$F = \frac{(A1 + A2)}{A3} \qquad \text{Equation (1)}$$

Exemplary embodiments of decomposition of a bio-signal into waveforms by the waveform decomposer 121 of FIG. 3 will be described in more detail with reference to FIGS. 5 to 8.

Figure 5:
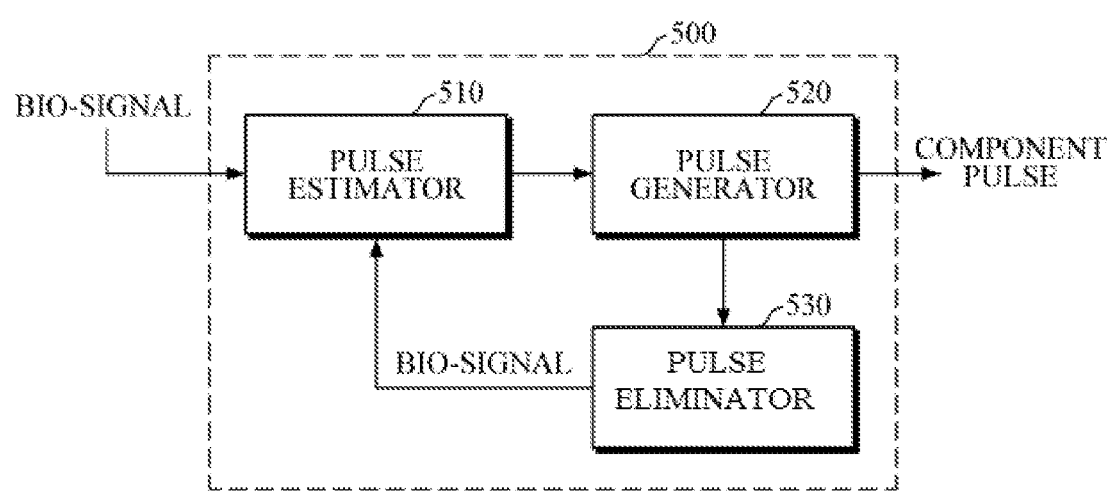
FIG. 5 is a block diagram illustrating an exemplary embodiment of a waveform decomposer of FIG. 3.

FIG. 5 is a block diagram illustrating an exemplary embodiment of the waveform decomposer of FIG. 3. FIG. 6 is a diagram for describing a method of waveform decomposition performed by the waveform decomposer of FIG. 5.

Referring to FIG. 5, the waveform decomposer 500 according to an exemplary embodiment includes a pulse estimator 510, a pulse generator 520, and a pulse eliminator 530.

Figure 6A:
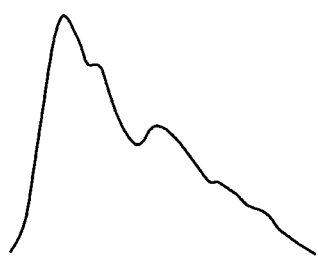
FIGS. 6A, 6B, 6C, and 6D are diagrams for describing a method of waveform decomposition performed by the waveform decomposer of FIG. 5.
Figure 6B:
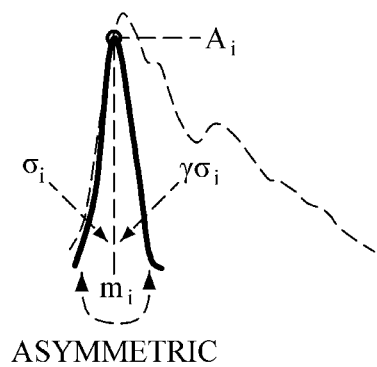

Referring to FIGS. 5 and 6A-6D, the pulse estimator 510 may estimate a component pulse to be decomposed on the basis of a bio-signal of FIG. 6A. In this case, the bio-signal may be a bio-signal to which the previously decomposed component pulse is applied. For example, the pulse estimator 510 may assume that the component pulse to be decomposed is a Gaussian waveform and may model a component pulse waveform function based on a Gaussian waveform function. In this case, since the Gaussian waveform function generally refers to a bilaterally symmetrical shape with respect to a time axis, the pulse estimator 510 according to the present exemplary embodiment may model the component pulse waveform function to be decomposed on the basis of the Gaussian waveform function, for which the pulse estimator 510 may model an asymmetric component pulse waveform function by Equation 2 below using an asymmetry factor γ which represents a degree of bilateral asymmetry with respect to a time axis, as shown in FIG. 6B.

$$g_i(t) = A_i \exp\left(-\frac{(t-m_i)^2}{2\sigma_i^2(t)}\right) + B_i \qquad \text{Equation (2)}$$

$$\sigma_i(t) = \begin{cases} \sigma_i, & \text{for } t \le m_i \\ \gamma\sigma_i, & \text{else} \end{cases}$$

Here, $g_i(t)$ represents the $i^{th}$ component pulse ($1 \le i \le L$, wherein L represents the number of component pulses to be decomposed on the basis of a bio-signal). t represents time, and $A_i$, $m_i$, $\sigma_i$ and $B_i$ represent the amplitude, mean time, standard deviation, and offset of the $i^{th}$ component pulse, respectively. Here, the offset may indicate how far the amplitude of the component pulse waveform is from a reference location.

As shown in Equation 2, the component pulse waveform modeled by the pulse estimator 510 may adjust the degree of bilateral asymmetry of the component pulse waveform with respect to the time axis by appropriately altering the asymmetry factor γ. For example, the asymmetry factor may be pre-set to a value between 1 and 2. If the asymmetry factor is set to "1", a bilaterally symmetric Gaussian waveform is obtained, and by gradually increasing the asymmetry factor to be greater than 1, the overall shape of a component pulse waveform increases steeply in the left side and decreases relatively gradually in the right side.

Then, when the component pulse waveform function is modeled by Equation 2, the pulse estimator 510 may estimate parameters of the component pulse waveform function, e.g., an amplitude $A_i$, a mean time $m_i$, a standard deviation $\sigma_i$ and an offset $B_i$. When a parameter of the component pulse waveform function is estimated, the pulse estimator 510 may estimate component pulses using the pre-set asymmetry factor.

Figure 6C:
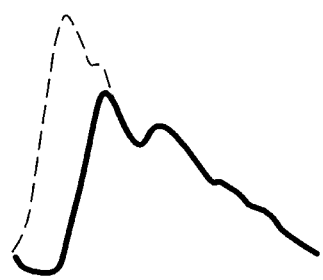

The pulse generator 520 may generate a component pulse signal from the estimated component pulses, and the pulse eliminator 530 may generate a new bio-signal by eliminating the component pulse signal from the bio-signal, as shown in FIG. 6C.

The pulse estimator 510, the pulse generator 520, and the pulse eliminator 530 may repeatedly perform the operations shown in FIG. 6A to 6C until a pre-set number of component pulses are generated.

Figure 6D:
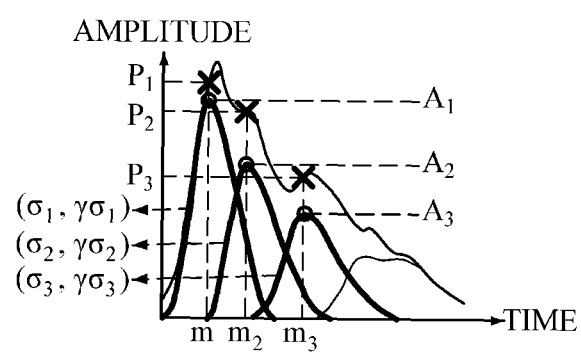

As shown in FIG. 6D, when a pre-set number (e.g., three) of component pulses are decomposed, characteristic points of each component pulse, for example, an amplitude $A_1$, $A_2$, and $A_3$, a mean time $m_1$, $m_2$, and $m_3$, a standard deviation $\sigma_1$, $\sigma_2$, and $\sigma_3$, and an amplitude $P_1$, $P_2$, and $P_3$ of an initial bio-signal may be obtained.

Hereinafter, an example of procedures of the pulse estimator 510 for estimating component pulses will be described.

The pulse estimator 510 first estimates parameters $A_1$, $m_1$, $\sigma_1$, and $B_1$ for the first (i=1) component pulse $g_1(t)$. The pulse estimator 510 obtains g'(t) and g''(t) respectively by the first-order and second-order differentiations of a bio-signal waveform function g(t) received from the bio-signal obtainer 110 of FIG. 1. For example, assuming that in the bio-signal waveform function g(t), a value of time t is a digital sample index which increases by 1, a first-order differential signal g'(t) when n=1 and a second differential signal g''(t) when n=2 may be obtained using Equation 3 below.

$$g^{(n)}(t) = g^{(n-1)}(t) - g^{(n-1)}(t-1) \qquad \text{Equation (3)}$$

Then, the pulse estimator 510 obtains time values $t_1$ and $t_2$ at a peak point in each waveform of the first-order differential function g'(t) and the second-order differential function g''(t). A relationship between the obtained time values $t_1$ and $t_2$ and the mean time $m_i$ and a standard deviation $\sigma_i$ of the component pulses may be represented by Equation 4 below.

$$t_1 = m_i - \sigma_i$$

$$t_2 = m_i - \sqrt{3}\sigma_i \qquad \text{Equation (4)}$$

The pulse estimator 510 may obtain the mean time $m_1$ and standard deviation $\sigma_1$ of the first component pulse using Equation 4, as shown in Equation 5.

$$m_1 = \frac{\sqrt{3}\,t_1 - t_2}{\sqrt{3} - 1} \qquad \text{Equation (5)}$$

$$\sigma_1 = \frac{t_1 - t_2}{\sqrt{3} - 1}$$

In this case, since the leading portion of the full waveform of the bio-signal g(t) may be similar to and overlap the left portion of the component pulse, it may be construed that the result of differentiation of the full waveform of the bio-signal g(t) within a range of time t which is smaller than the mean time $m_i$ is similar to the result of differentiation of the left portion of the component pulse. Accordingly, it can be seen that Equation 4 is verified when a point in time is obtained at which the result of the second-order and third-order differentiations of the $A_i \exp(-(t-m_i)^2/(2\sigma_i^2)) + B_i$ of Equation 2, which is the function that corresponds to the left portion of the component pulse waveform, becomes 0.

Then, the pulse estimator 510 may estimate the amplitude $A_1$ and offset $B_1$ of the first component pulse $g_1(t)$ using the amplitudes $g(t_1)$ and $g(t_2)$ of the bio-signal $g(t)$ which correspond to the obtained time point $t_1$ and $t_2$, respectively. In this case, the relationship between the amplitudes $g(t_1)$ and $g(t_2)$ of the bio-signal $g(t)$ and the amplitude $A_1$ and offset $B_1$ of the first component pulse $g_1(t)$ may be expressed by Equation 6 below.

$$g(t_1) \cong g_i(t_1) = A_i \exp\left(-\frac{(t_i - m_i)^2}{2\sigma_i^2}\right) + B_i = A_i \exp(-1/2) + B_i \quad \text{Equation (6)}$$

$$g(t_2) \cong g_i(t_2) = A_i \exp\left(-\frac{(t_2 - m_i)^2}{2\sigma_i^2}\right) + B_i = A_i \exp(-3/2) + B_i$$

In Equation 6, $g(t_1) \cong g_i(t_1)$ and $g(t_2) \cong g_i(t_2)$ indicate that the bio-signal waveform $g(t)$ and $g_i(t)$ are similar to each other in shape within a range of time t which is smaller than the mean time $m_i$. By using Equation 6, the amplitude $A_1$ and offset $B_1$ of the first component pulse $g_1(t)$ may be estimated as shown in Equation 7.

$$A_1 = \frac{g_1(t_1) - g_1(t_2)}{\exp\left(-\frac{1}{2}\right) - \exp\left(-\frac{3}{2}\right)} \quad \text{Equation (7)}$$

$$B_1 = \frac{-\exp\left(-\frac{3}{2}\right)g_1(t_1) + \exp\left(-\frac{1}{2}\right)g_1(t_2)}{\exp\left(-\frac{1}{2}\right) - \exp\left(-\frac{3}{2}\right)}$$

The pulse estimator 510 may estimate parameters of the first component pulse as described above and may estimate the first component pulse $g_1(t)$ using the pre-set asymmetry factor.

When the pulse estimator 510 estimates the parameters of the component pulse waveform function, the pulse generator 520 generates the first component pulse signal using the parameters.

When the component pulse signal is generated, the pulse eliminator 530 may generate a bio-signal for estimating the subsequent component pulse by eliminating the generated component pulse from the current bio-signal. For example, as shown in Equation 8 below, the pulse eliminator 530 may generate a new bio-signal $g(t)$ for estimating the second component pulse $g_2(t)$ by eliminating the first component pulse signal $g_1(t)$ from the initial bio-signal $g(t)$ received from the bio-signal obtainer 110 of FIG. 1.

$$g(t) = g(t) - g_1(t) \quad \text{Equation (8)}$$

Meanwhile, when the component pulse is generated, the pulse estimator 510 determines whether the total number of generated component pulses satisfies the pre-set number (e.g., 3) or not, and if not, may estimate the subsequent component pulse.

Hereinafter, the procedures of the pulse estimator 510 for estimating the second and the subsequent component pulses ($i \geq 2$) will be described. As described above, it is assumed that the leading portion of the bio-signal from which the previously generated component pulse has been eliminated is similar to the left portion of the component pulse to be currently estimated. In addition, it is seen that during the elimination process of Equation 8 for the first (i=1) component pulse, the offset $B_1$ of the first component pulse is eliminated from the full bio-signal. Thus, since offsets of component pulses that constitute one bio-signal are generally the same as and/or similar to each other, it may be seen that DC components of the second and the subsequent component pulses that are to be decomposed using the bio-signal from which a non-zero DC component of the first component pulse has been eliminated are 0. That is, it is assumed that the offsets $B_i$ of the second and the subsequent component pulses are 0.

When the pulse generator 520 generates an $(i-1)^{th}$ component pulse and the pulse eliminator 530 generates a new bio-signal $g(t)$ that is generated by eliminating the $(i-1)^{th}$ component pulse from the current bio-signal, the pulse estimator 510 may estimate the $i^{th}$ component pulse $g_i(t)$ using Equation 2 above.

For example, the pulse estimator 510 obtains time $t_i$ at a peak point by first-order differentiation of the new bio-signal $g(t)$. When time $t_i$ at a peak point is obtained, the first relational equation in Equation 4 can be derived. In this case, since the offsets Bi of the second and the subsequent component pulses are assumed to be 0, when the first expression of Equation 4 is applied to the bio-signal $g(t)$, that is, when the first expression in Equation 6 is used, a relational expression as shown in Equation 9 below may be obtained.

$$g(t_1) = A_i \exp(-0.5) \quad \text{Equation (9)}$$

The pulse estimator 510 may obtain the amplitude $A_i$ of the $i^{th}$ component pulse using both the first expression in Equation 4 and Equation 9.

Then, in order to estimate the mean time $m_i$ and standard deviation $\sigma_i$ of the $i^{th}$ component pulse, the pulse estimator 510 may use time $t_{offset}$ obtained by Equation 10 below, rather than using time $t_1$ at an upper peak point, wherein time $t_{offset}$ $2\sigma_i$ away from the mean time $m_i$ to the left.

$$t_{offset} = m_i - 2\sigma_i \quad \text{Equation (10)}$$

By applying the obtained time $t_{offset}$ to $t_i$ in the first expression of Equation 6, a relational equation as shown in Equation 11 below may be obtained, wherein the amplitude $A_1$ is obtained by Equation 9 so that it is possible to compute $t_{offset}$ that satisfies said expression.

$$g(t_{offset}) = A_1 \exp(-2) \quad \text{Equation (11)}$$

The above Equations may be summarized as shown in Equation 12, and the pulse estimator 510 may estimate parameters $A_i$, $m_i$, $\sigma_i$, and $B_i$ of the $i^{th}$ component pulse ($i \geq 2$) using Equation 12.

$$m_i = 2t_1 - t_{offset}$$

$$\sigma_i = t_1 - t_{offset}$$

$$A_i = g(t_i) / \exp(-0.5)$$

$$B_i = 0 \quad \text{Equation (12)}$$

When the parameters of the $i^{th}$ component pulse waveform function are estimated as described above, the pulse estimator 510 may estimate the $i^{th}$ component pulse using the pre-set asymmetry factor.

Figure 7:
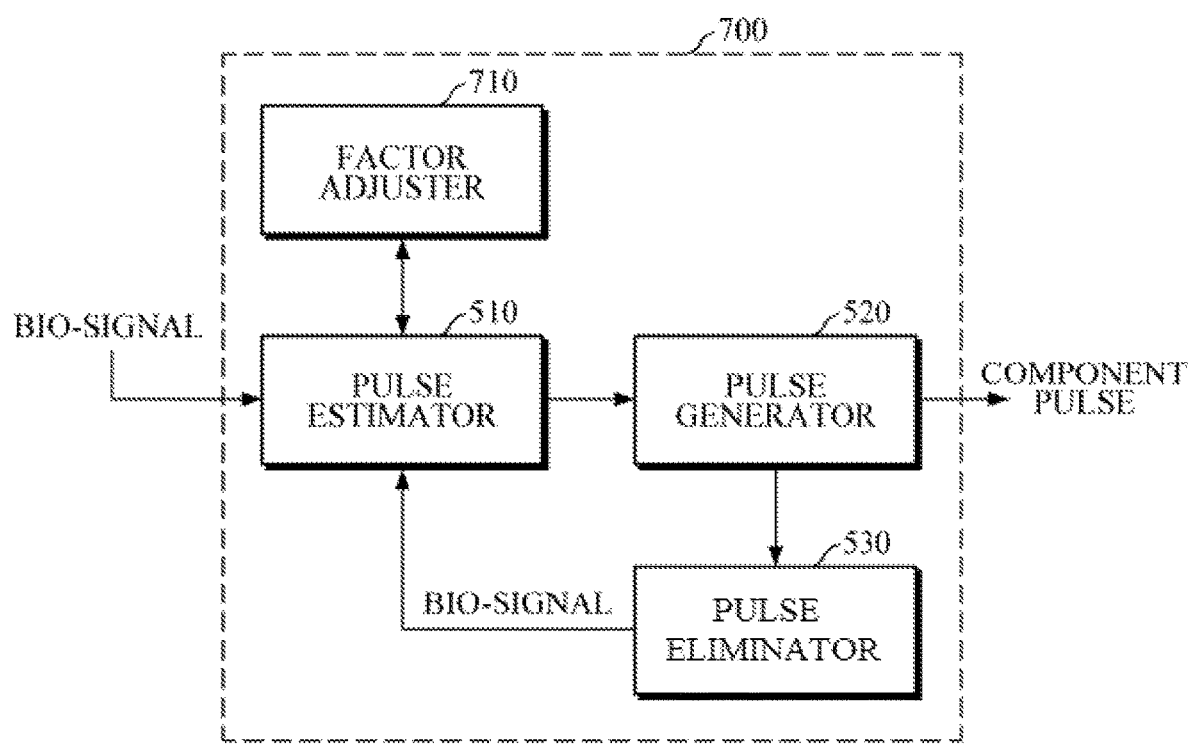
FIG. 7 is a block diagram illustrating another exemplary embodiment of the waveform decomposer of FIG. 3.
Figure 8:
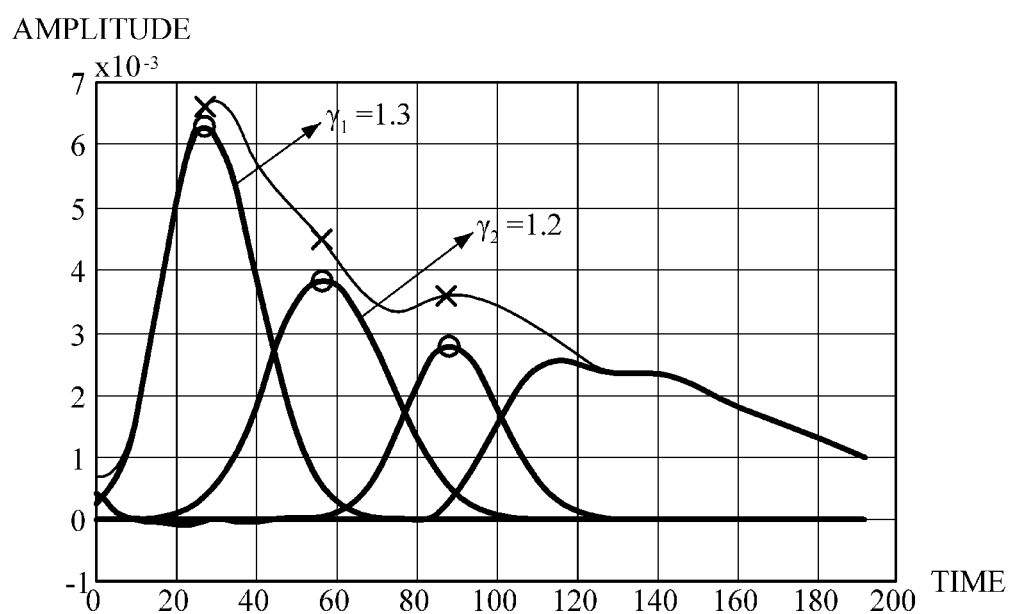
FIG. 8 is a graph for describing a method of asymmetry factor adjustment performed by a factor adjuster of FIG. 7.

FIG. 7 is a block diagram illustrating another exemplary embodiment of the waveform decomposer of FIG. 3. FIG. 8 is a graph for describing a method of asymmetry factor adjustment performed by a factor adjuster of FIG. 7.

Referring to FIG. 7, the waveform decomposer 700 in accordance with another exemplary embodiment includes a pulse estimator 510, a pulse generator 520, a pulse eliminator 530, and a factor adjuster 710.

The pulse estimator 510, the pulse generator 520 and the pulse eliminator 530 are already described in detail with reference to FIG. 5, and thus the description herein will focus on the configuration of the factor adjuster 710.

According to the present exemplary embodiment, the factor adjuster 710 may adjust a pre-set asymmetry factor adaptively to each component pulse. As described above, the asymmetry factor makes a component pulse waveform bilaterally asymmetric with respect to a time axis, and it is possible to accurately estimate each waveform of component pulses to be decomposed by adjusting the asymmetry factor.

For example, when the pulse estimator 510 estimates parameters by modeling the $i^{th}$ component pulse function and estimates the $i^{th}$ component pulse using the pre-set asymmetry factor, the factor adjuster 710 may adjust the asymmetry factor on the basis of a bio-signal from which the $i^{th}$ component pulse has been eliminated. When the asymmetry factor is adjusted, the pulse estimator 510 may re-estimate the $i^{th}$ component pulse using the adjusted asymmetry factor, and the factor adjuster 710 may adjust the asymmetry factor for the estimated $i^{th}$ component pulse. As such, the procedures for adjusting the asymmetry factor for the $i^{th}$ component pulse may be repeatedly performed until a predetermined criterion is satisfied.

The factor adjuster 710 may obtain the mean time $m_{i+1}$ and time $T_{i+1}$ at a peak point from the bio-signal from which the estimated $i^{th}$ component pulse has been eliminated, and, when the mean time $m_{i+1}$ is smaller than the time $T_{i+1}$ at a peak point, may increase the asymmetry factor by an adjustment value. In this case, the factor adjuster 710 may determine a local minimum point of the second-order differentiation of the bio-signal as the time $T_{i+1}$ at a peak point.

Meanwhile, reference information, such as an initial value, an adjusted width, or information indicating whether to adjust the asymmetry factor for each component pulse, may be stored in advance in a storage device of the feature extraction apparatus 100. The factor adjuster 710 may determine whether to adjust the asymmetry factor for each component pulse by checking the pre-set reference information and perform the above-described adjustment of the asymmetry factor. In this case, the smaller the adjustment value is, the more precise the adjustment of the asymmetry factor is, whereas the complexity of adjustment increases, and hence the adjustment value may be set to be an appropriate value, for example, 0.1.

Referring to FIG. 8, it is seen that the respective asymmetry factors $\gamma_1$ and $\gamma_2$ for the first component pulse and the second component pulse are adjusted from the initial value, i.e., 1, to 1.3 and 1.2, respectively. As the asymmetry factor moves closer to 1, a pulse becomes more bilaterally asymmetric, and thus the first component pulse becomes more asymmetric than the second component pulse.

Figure 9:
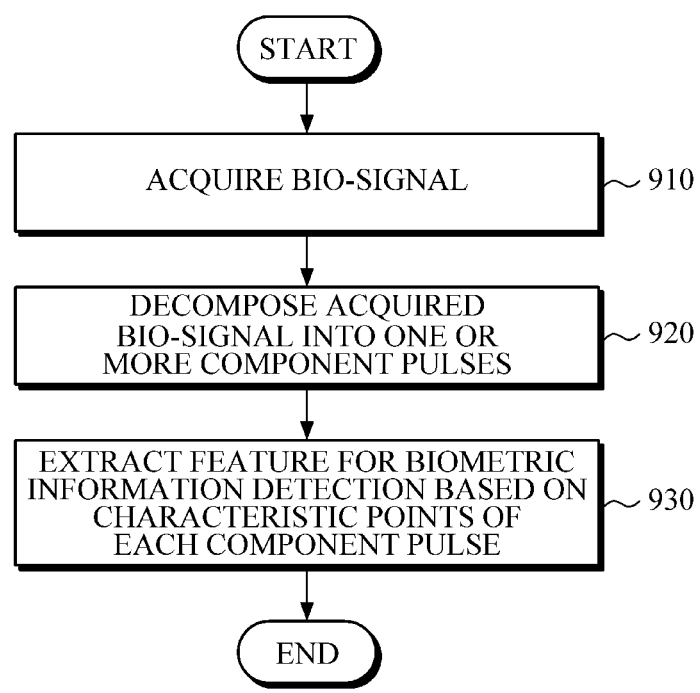
FIG. 9 is a flowchart illustrating a method of feature extraction according to an exemplary embodiment.

FIG. 9 is a flowchart illustrating a method of feature extraction according to an exemplary embodiment.

FIG. 9 illustrates an exemplary embodiment of a method of feature extraction performed by feature extraction apparatuses. For illustrative purposes, the following description refers to the feature extraction apparatuses 100 and 200 of FIGS. 1 and 2 as performing the method shown in FIG. 9, although exemplary embodiments are not limited thereto. In operation 910, the feature extraction apparatuses 100 and 200 may obtain a bio-signal in order to extract a feature used for biometric information detection. In this case, for example, the feature extraction apparatus may include a sensor to acquire a bio-signal, wherein the sensor emits light onto a user's skin and detects light returning from the skin and obtains a bio-signal. In another example, the bio-signal may be received from an external device, for example, a biometric information detection apparatus including a sensor for acquiring the bio-signal.

In operation 920, the bio-signal is decomposed into one or more component pulses. In this case, the number of component pulses to be decomposed on the basis of a bio-signal may be pre-set according to the shape of the bio-signal waveform, the type of biometric information, and the like. Operation 920 will be described in more detail with reference to FIGS. 10 and 11.

Then, in operation 930, when one or more component pulses are decomposed, characteristic points are obtained from each component pulse, and a feature used for biometric information detection is extracted using the obtained characteristic points. In this case, the characteristic points may include the time, amplitude, and standard deviation of each component pulse and the amplitudes of the full bio-signal that correspond to the time of each component pulse. In addition, the feature used for biometric information detection may be extracted by combining the characteristic points as shown in Equation 1.

Figure 10:
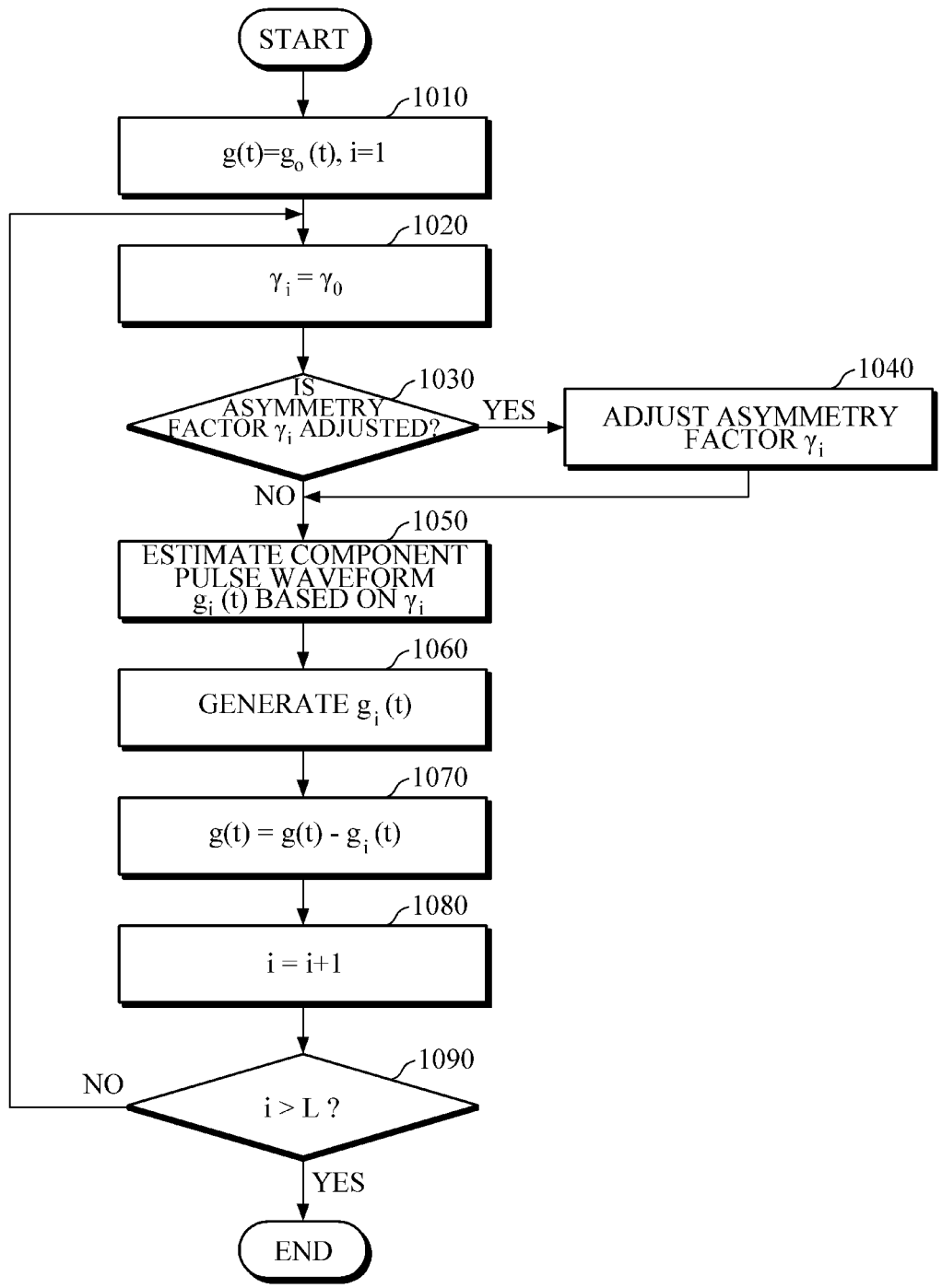
FIG. 10 is a flowchart illustrating an exemplary embodiment of an operation of waveform decomposition of FIG. 9.
Figure 11:
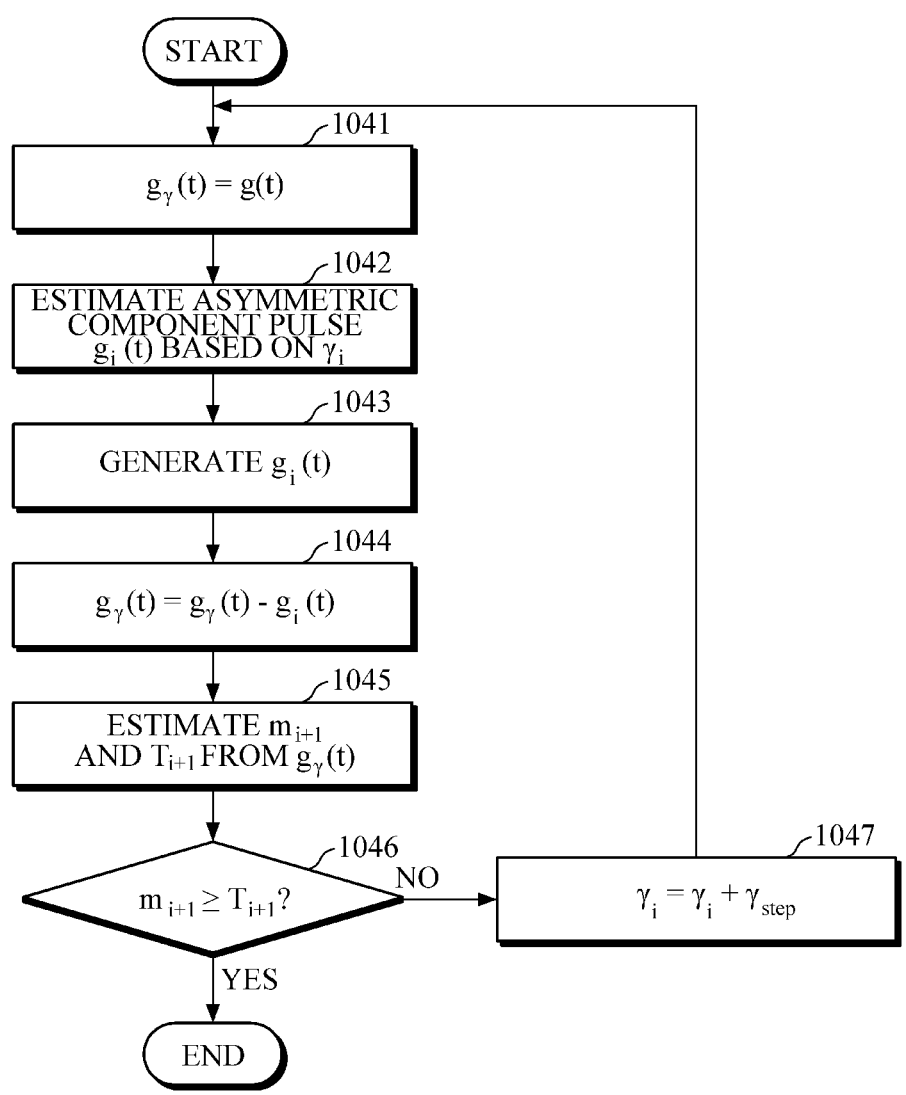
FIG. 11 is a flowchart illustrating an exemplary embodiment of an operation of asymmetry factor adjustment of FIG. 10.

FIG. 10 is a flowchart illustrating an exemplary embodiment of waveform decomposition shown in operation 920 of FIG. 9. FIG. 11 is a flowchart illustrating an exemplary embodiment of asymmetry factor adjustment shown in operation 1040 of FIG. 10.

Referring to FIG. 10, in operation 1010, when decomposing a bio-signal waveform into one or more component pulses, the initial bio-signal $g_0(t)$ obtained in operation 910 is set as g(t) and a component pulse index i for decomposition of the first component pulse is set to "1".

Then, in operation 1020, an asymmetry factor $\gamma_i$ for estimation of the $i^{th}$ asymmetric component pulse waveform is set as an initial value $\gamma_0$.

Then, in operation 1030, it is determined whether the asymmetry factor $\gamma_i$ for the $i^{th}$ component pulse is adjusted or not. In this case, the determination as to whether the asymmetry factor for each component pulse is adjusted may be made by checking a pre-set criterion.

Thereafter, in operation 1040, in response to a determination in operation 1030 that the asymmetry factor for the $i^{th}$ component pulse is adjusted, the asymmetry factor $\gamma_i$ is adjusted.

Operation 1040 is described in more detail with reference to FIG. 11. First, in operation 1041, the bio-signal g(t) for estimation of the $i^{th}$ component pulse is set as bio-signal $g_\gamma(t)$ for asymmetry factor adjustment.

Then, in operation 1042, the $i^{th}$ asymmetric component pulse $g_i(t)$ is estimated using the original asymmetry factor $\gamma_i$ before adjustment.

Then, in operation 1043, the $i^{th}$ component pulse $g_i(t)$ is generated, and in operation 1044, $g_i(t)$ is eliminated from the bio-signal $g_\gamma(t)$, so as to set a new bio-signal $g_\gamma(t)$.

Thereafter, in operation 1045, the mean time $m_{i+1}$ and time $T_{i+1}$ at a peak point are estimated from the new bio-signal $g_\gamma(t)$. In this case, time at a local minimum point of the second-order differentiation of the bio-signal $g_\gamma(t)$ may be set as the time $T_{i+1}$ at a peak point.

Then, in operation 1046, the mean time $m_{i+1}$ and the time $T_{i+1}$ at a peak point are compared with each other, and when the mean time $m_{i+1}$ is equal to or greater than the time $T_{i+1}$ at a peak point, the asymmetry factor $\gamma_i$ is not adjusted. Otherwise, the asymmetry factor $\gamma_i$ is increased by an adjustment amount $\gamma_{step}$, and operation 1041 and the subsequent operations are repeatedly performed.

Referring back to FIG. 10, when the asymmetry factor to be applied to the $i^{th}$ component pulse is determined, in operation 1050, the component pulse waveform $g_i(t)$ is estimated, and in operation 1060, a component pulse signal is generated.

Then, in operation 1070, the generated component pulse $g_i(t)$ is eliminated from the bio-signal g(t), and the elimination result is set as a new bio-signal g(t) for estimation of the subsequent component pulse.

Thereafter, in operation 1080, the component pulse index i is increased by 1. Then, in operation 1090, i is compared with the number L of component pulses to be decomposed, and if i is not greater than L, the flow proceeds to operation 1020 for estimating the subsequent component. Otherwise, the procedure is terminated since decomposition of all component pulses is completed.

Figure 12:
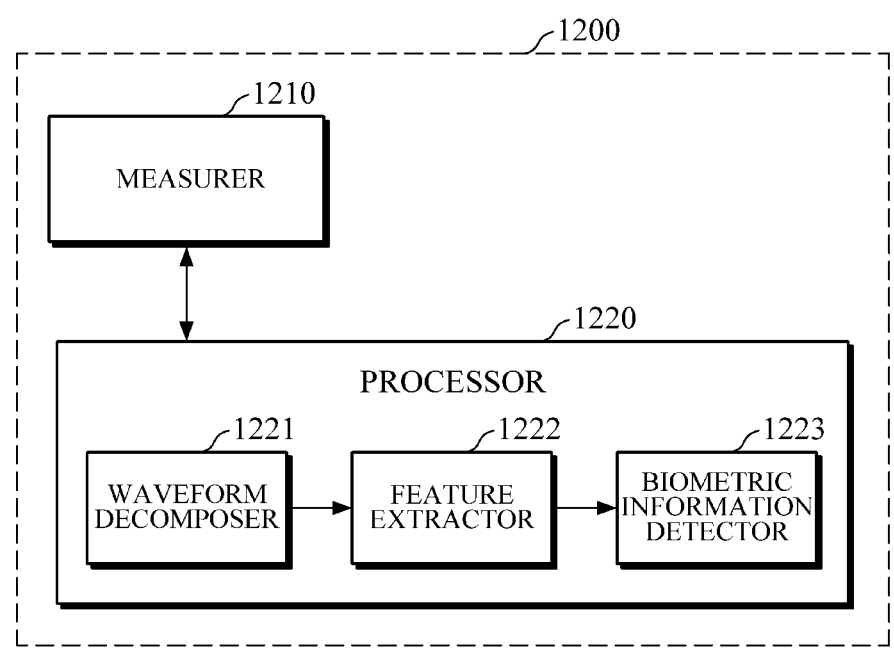
FIG. 12 is a block diagram illustrating a biometric information detection apparatus according to an exemplary embodiment.

FIG. 12 is a block diagram illustrating a biometric information detection apparatus according to an exemplary embodiment. The biometric information detection apparatus 1200 according to the present exemplary embodiment may be an apparatus which employs the aforementioned feature extraction techniques and detects biometric information, such as blood pressure. For example, the biometric information detection apparatus 1200 may be a cuffless indirect blood pressure measurement apparatus and may be implemented by a device, such as a wearable device. The wearable device may be implemented as a wristwatch type, a bracelet type, a wrist band type, or the like. However, the type of wearable device is not limited thereto and may be implemented as a ring-type, a glasses-type, a hairband-type, or the like.

Referring to FIG. 12, the biometric information detection apparatus 1200 includes a measurer 1210 and a processor 1220, wherein the processor 1220 includes a waveform decomposer 1221, a feature extractor 1222, and a biometric information detector 1223.

The measurer 1210 may include a light source which is operated to emit light onto a user's skin in response to a predetermined control signal and a detector which detects light returning from the user's skin, and the measurer 1210 may measure a bio-signal using the detected light. In this case, the user's skin area to which the light is emitted may be an area of the wrist skin surface close to the radial artery. When the pulse wave is measured at the skin surface of the user's wrist under which the radial artery passes, the influence of external factors causing errors in measurement, such as the thickness of the skin tissue inside the wrist and the like, may be relatively small. It is known that blood pressure can be more accurately measured from the radial artery than from the other vessels in the wrist. However, the skin area is not limited to the above description and may be a distal area of the human body with a high density of blood vessels, such as a finger, a toe, or the like.

In this case, when a biometric information detection request is received from the user through an interface module, the processor 1220 may generate a control signal to control the measurer 1220. In this case, the interface module may include, but is not limited to including, a display, a microphone, a speaker, and a haptic device. The processor 1020 may perform various functions for interaction with a user through the interface module. For example, the processor 1020 may present a graphic user interface on a display in order to enable the user to input a control instruction by touching the display. In another example, the processor 1020 may be equipped with a conversational agent function and a voice recognition function in order to enable the user to perform interaction, such as vocally input of a control instruction through a microphone, a speaker, and the like.

The waveform decomposer 1221 and the feature extractor 1222 of the processor 1220 may perform the same functions as the waveform decomposer 121 and the feature extractor 122 included in the feature extraction apparatuses 100 and 200, which are described with reference to FIG. 3, and hence detailed descriptions thereof will be omitted.

The biometric information detector 1223 may detect biometric information on the basis of a feature extracted by the feature extractor 122. For example, since the feature estimated using Equation 1 may be correlated with blood pressure, the biometric information detector 1223 may generate a correlation model that represents a correlation and generate blood pressure using the generated correlation model. In this case, the correlation model may be an equation which represents the correlation between the feature and the blood pressure, although is not limited thereto, and the correlation model may instead be defined in the form of a matching table or other mathematical tool for showing a correlation.

In this case, the biometric information detector 1223 may control the measurer 1210 to measure a bio-signal at predetermined time intervals (e.g., 15 minutes) for a predetermined time period (e.g., 5 hours) and may generate the correlation model by deriving the relationship between the feature and the actual blood pressure on the basis of the measured bio-signal used as training data.

Meanwhile, the processor 1220 may provide the user with detected blood pressure information, and additional information, such as a risk score, warning information, or the like through the interface module. For example, the blood pressure information or information on a risk score regarding the health status may be presented on the display and provided to the user, wherein a different predefined color is used for each risk score, enabling the user to easily recognize his or her health status. In addition, a warning message predefined according to the risk score may be presented on the display. The blood pressure, the risk score and the warning information may be output in an audible manner using a speaker. Moreover, if a haptic device is mounted or connected, the risk score or the warning information may be provided to the user through tactile sensation or vibration. However, the exemplary embodiments are not limited to the above examples, and the information may be provided to the user using the combination of two or more visual and non-visual methods according to the type of interface module, the performance of the apparatus, and the purpose of the provision of information.

Figure 13:
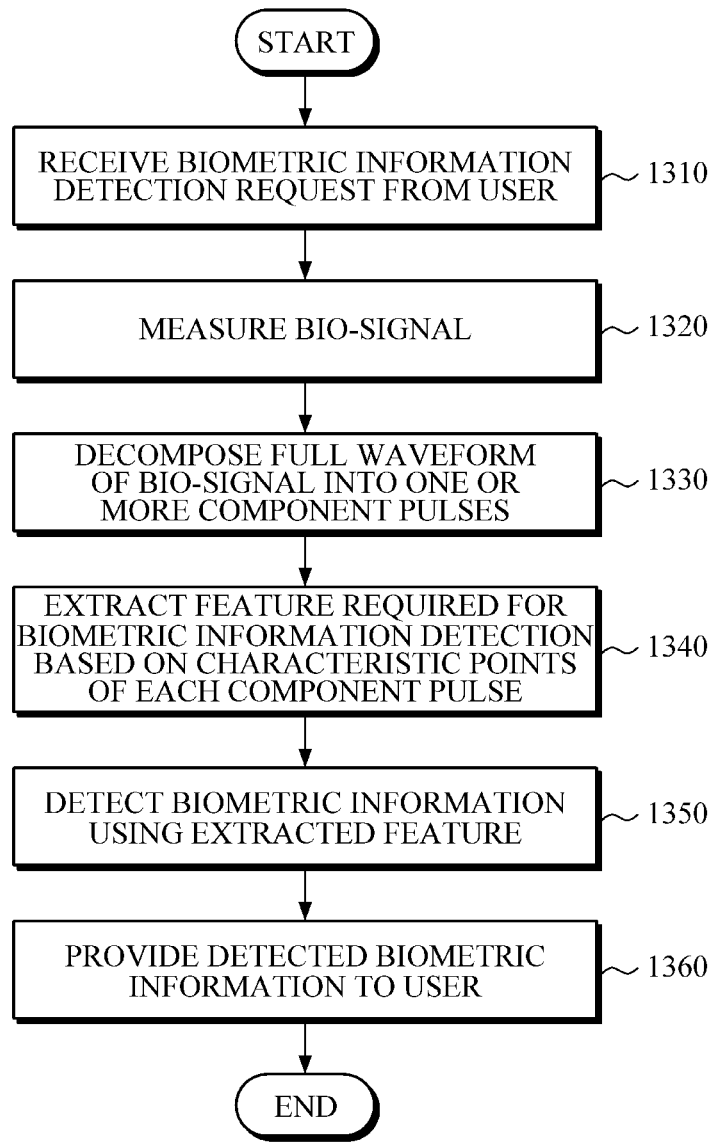
FIG. 13 is a flowchart illustrating a method of biometric information detection according to an exemplary embodiment.

FIG. 13 is a flowchart illustrating a method of biometric information detection according to an exemplary embodiment.

The method shown in FIG. 13 may be performed, for example, by the biometric information detection apparatus 1200 of FIG. 12, although is not limited thereto.

First, in operation 1310, a biometric information detection request is received from a user.

Then, in operation 1320, a bio-signal of the user is measured by controlling a sensor.

In operation 1330, or more component pulses are decomposed on the basis of the full waveform of the measured bio-signal. In this case, each time a sequential component pulse is generated, the bio-signal is updated by eliminating the component pulse therefrom.

Then, in operation 1340, characteristic points are obtained from each of the decomposed component pulses and a feature used for biometric information detection is extracted based on the obtained characteristic points. In this case, the characteristic points may be obtained from each component pulse, and may include information about, for example, the amplitude, time, and standard deviation of each component pulse. In addition, the feature may be extracted by combining the obtained characteristic points.

Thereafter, in operation 1350, the biometric information is detected using the extracted feature. In this case, the blood pressure that corresponds to the extracted feature may be detected as the final result using a correlation model which represents the correlation between the feature and the biometric information, for example, the blood pressure.

Then, in operation 1360, the detected biometric information is provided to the user. In this case, biometric information, such as the detected blood pressure, an alarm, or a warning message may be provided using an interface module. Also, the information may be provided to the user using various predefined visual or non-visual mechanisms.

Figure 14:
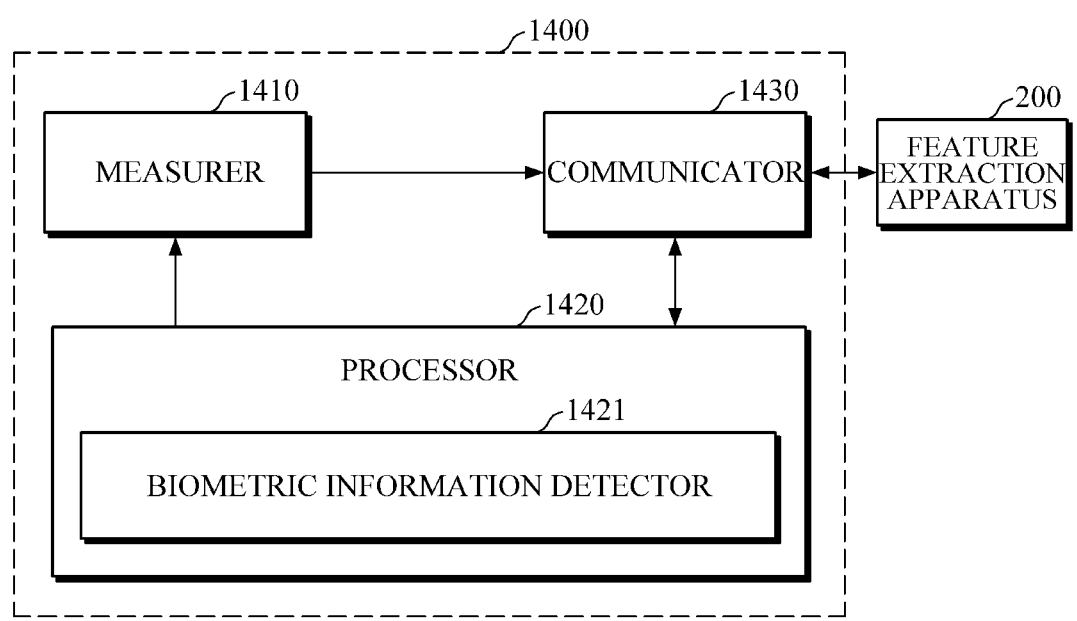
FIG. 14 is a block diagram illustrating a biometric information detection apparatus according to another exemplary embodiment.

FIG. 14 is a block diagram illustrating a biometric information detection apparatus according to another exemplary embodiment.

Referring to FIG. 14, the biometric information detection apparatus 1400 in accordance with another exemplary embodiment includes a measurer 1410, a processor 1420, and a communicator 1430.

The measurer 1410 acquires a bio-signal from a user under the control of the processor 1420. In this case, the measurer 1410 may be the same as the measurer 121 of FIG. 12, and hence a detailed description thereof will not be repeated.

The processor 1420 may control the measurer 1410 by generating a control signal when receiving a biometric information detection request from a user, and, when the bio-signal is measured, may control the communicator 1430 to transmit the bio-signal and feature extraction request information to a feature extraction apparatus 200.

In addition, the processor 1420 may include a biometric information detector 1421. When the processor 1420 receives each component pulse decomposed on the basis of the bio-signal and characteristic points and feature information of each component pulse from the feature extraction apparatus 200 through the communicator 1430, the biometric information detector 1421 may detect the biometric information using the received feature information.

Further, the processor 1420 may provide information related to the detected biometric information to the user, as described above.

Meanwhile, the biometric information detection apparatus 1400 in accordance with the exemplary embodiments includes both an exemplary embodiment in which the measurer 1410, the processor 1420, and the communicator 1430 are implemented as a single hardware device and another exemplary embodiment in which the measurer 1410 is implemented as a separate hardware device. In a case in which the measurer 1410 is implemented as a separate hardware device, the measurer 1410 may be provided in a wearable device, while the processor 1420 and the communicator 1430 may be provided in a mobile terminal device that the user carries, such as a smartphone or a tablet PC.

FIGS. 15A, 15B, 15C, and 15D are diagrams for describing a wearable device according to an exemplary embodiment. The various exemplary embodiments of the feature extraction apparatus and the biometric information detection apparatus described above may be equipped in a smart band-type wearable device. However, this is merely one example for convenience of description, and thus the exemplary embodiments should not be construed as being limited to being applied in the smart band-type wearable device.

Referring to FIGS. 15A to 15D, the wearable device 1500 includes a main body 1510 and a strap consisting of strap members 1521 and 1522.

The strap may be formed to be flexible and may be bent to encircle the user's wrist or to be separated from the wrist. In this case, a battery for power supply to the wearable device may be embedded in the main body 1510 or the strap members 1521 and 1522.

In addition, in the main body 1510 of the wearable device 1500, a measurer 1511 which measures a bio-signal by emitting light onto a user's skin and detecting light scattered from the skin and a processor 1512 which detects biometric information of the user using the bio-signal measured by the measurer 1511 may be embedded.

The measurer 1511 may be mounted on a lower portion of the main body 1510, e.g., a portion that comes in contact with the user's wrist, and may include a light source which emits light onto the user's skin in response to a control signal of the processor 1512 and one or more detectors which are arranged side by side at different distances from the light source and detect light returning from the user's skin.

The processor 1512 may generate the control signal according to a user's request and control the measurer 1511. In addition, the processor 1512 may receive bio-signal data measured from the measurer 1511 and detect biometric information using the bio-signal data. For example, the processor 1512 may decompose the bio-signal into one or more component pulses, as described above, and extract a feature utilizing characteristic points of each of the decomposed component pulses. Moreover, the processor 1512 may detect the biometric information using the extracted feature. At this time, the processor 1512 may estimate the biometric information using a correlation model which represents the correlation between the extracted feature and the biometric information.

Further, the processor 1512 may manage the detected biometric information, for example, blood-pressure history information, biometric information utilized in blood pressure measurement, and each component pulse decomposed from the biometric information, by storing the detected biometric information in a storage device. Also, the processor 1512 may generate additional information used for user's health care, such as an alarm or warning information related to the detected biometric information, or changes in the health status of the user, and manage the additional information by storing the additional information in the storage device.

The wearable device 1500 may further include a controller 1515 and a display 1514, which are both mounted in the main body 1510.

The controller 1515 may receive the user's control instruction and forward the control instruction to the processor 1512, and may include a power button for the user to turn power of the wearable device 1500 on and off.

The display 1514 may provide the user with a variety of information related to the detected biometric information under the control of the processor 1512. For example, the display 1514 may display additional information, such as a measured blood pressure, an alarm, or a warning message, to the user in various visual or non-visual manners.

Figure 15A:
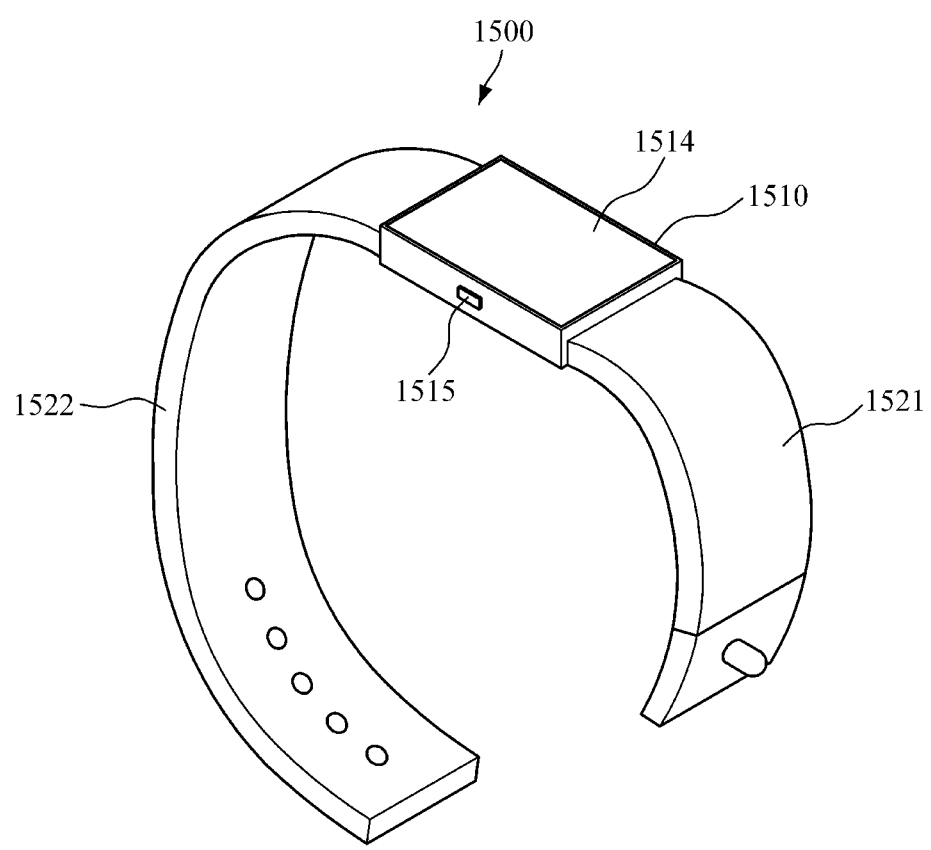
FIGS. 15A, 15B, 15C, and 15D are diagrams for describing a wearable device according to an exemplary embodiment.
Figure 15B:
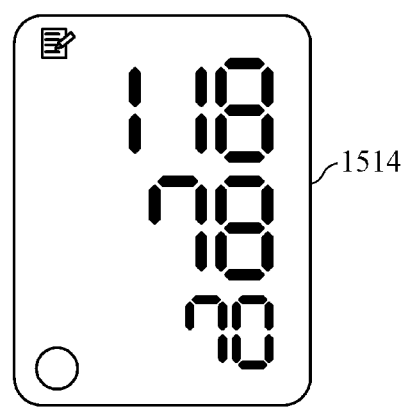
Figure 15C:
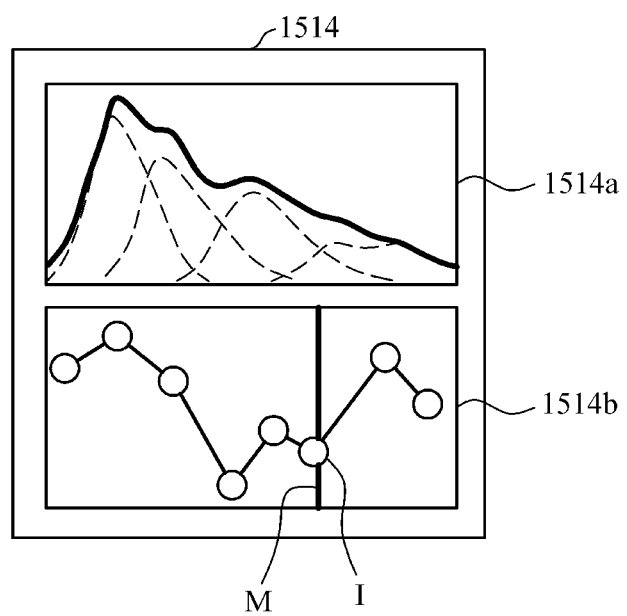
Figure 15D:
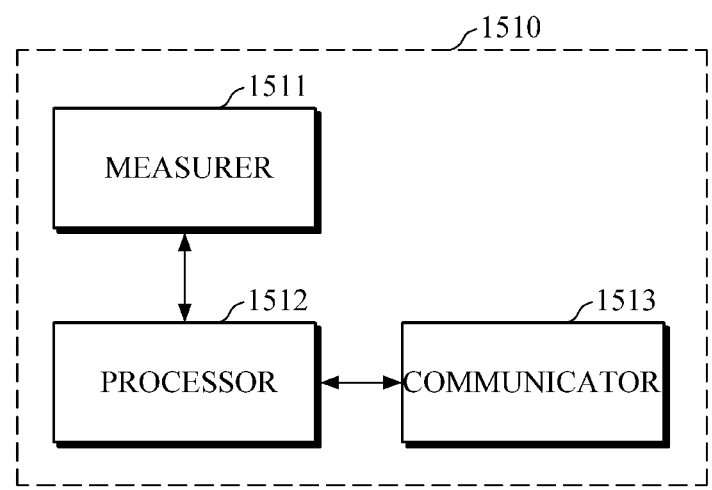

For example, when blood pressure is detected according to the user's request, the display 1514 may present the detected blood pressure information, as shown in FIG. 15B. In addition, when the user manipulates the controller 1515 or touches the display 1514 so as to request detailed information, the display 1514 may present a variety of detailed information, as shown in FIG. 15C. The display 1514 may include a first section 1514b and a second section 1514a and may present the detected blood pressure information, as shown in FIG. 15B, in the first section 1514b or present changes in the blood pressure in the form of graph, as shown in FIG. 15C.

In this case, the display 1514 may present a mark M that indicates currently selected blood pressure information I in the first section 1514b. Although the mark M is presented as a vertical line, the shape of the mark is not limited thereto and may be presented in various shapes, such as a circle, a polygon, a rectangle, an arrow indicating a position, and the like. When changes in the blood pressure are presented in the first section 1514b, the user may select one portion of blood pressure information by touching the display 1514 or by horizontally moving the graph until the blood pressure information of interest is aligned with the mark M. As such, when the user selects the blood pressure information from the first section 1514b, in response to the selection, the display 1514 may present the bio-signal used to detect the selected blood pressure information I and each component pulse decomposed from the bio-signal in the second section 1514a.

Accordingly, the user may easily recognize the changes in the blood pressure and intuitively understand changes in the bio-signal and the component pulses according to the changes in the blood pressure.

In addition, the main body 1510 may further include a communicator 1513 in an interior area thereof in order to communicate with an external device, such as a portable terminal of the user.

The communicator 1513 may transmit information to the user's portable terminal having a relatively high computing performance so as to provide the user with the information.

The current exemplary embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the recording medium may be implemented in the form of a carrier wave such as an Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A feature extraction apparatus configured to perform biometric information detection, the feature extraction apparatus comprising:
   a sensor configured to acquire a bio-signal; and
   a processor configured to:
      adjust an asymmetry factor for component pulses of the bio-signal;
      decompose a waveform of the acquired bio-signal into the component pulses based on adjusting the asymmetry factor; and
      extract a feature for the biometric information detection based on characteristic points of the component pulses.

2. The feature extraction apparatus of claim 1, wherein the processor is configured to:
   obtain a subsequent component pulse based on a new bio-signal generated based on one of the component pulses.

3. The feature extraction apparatus of claim 2, wherein the processor is configured to:
   estimate a given component pulse to be decomposed, among the component pulses, based on the waveform of the bio-signal and thereby generate an estimation result; and
   generate the given component pulse based on the estimation result.

4. The feature extraction apparatus of claim 3, wherein the processor is configured to, when the given component pulse is generated, eliminate the generated component pulse from the bio-signal, and when a number of generated component pulses is smaller than a pre-set number, estimate another subsequent component pulse based on another new bio-signal generated by eliminating the generated component pulse.

5. The feature extraction apparatus of claim 3, wherein the processor is configured to model a component pulse waveform function based on the waveform of the acquired bio-signal and estimate parameters of the component pulse waveform function.

6. The feature extraction apparatus of claim 5, wherein the processor is configured to model the component pulse waveform function to be bilaterally asymmetric with respect to a time axis, based on a Gaussian waveform function and the asymmetry factor.

7. The feature extraction apparatus of claim 6, wherein the processor is configured to, when the given component pulse is estimated based on a current bio-signal and the asymmetry factor, adjust the asymmetry factor based on a new bio-signal generated by eliminating the estimated component pulse from the current bio-signal, and re estimate the given component pulse based on the current bio-signal and the adjusted asymmetry factor.

8. The feature extraction apparatus of claim 7, wherein the processor is configured to adjust the asymmetry factor based on a determination that a mean time period of the eliminated component pulse is smaller than a time period at a peak point.

9. The feature extraction apparatus of claim 1, wherein the processor is configured to extract the feature for the biometric information detection based on characteristic points which include one or more of time, an amplitude, a standard deviation, and an offset of the decomposed component pulses.

10. The feature extraction apparatus of claim 1, wherein the sensor is configured to acquire the bio-signal by emitting light onto a user's skin and detecting light returning from the user's skin.

11. The feature extraction apparatus of claim 1, further comprising a communication interface configured to receive the bio-signal from a biometric information detection apparatus, forward the bio-signal to the sensor and transmit a result of processing based on the received bio-signal to the biometric information detection apparatus.

12. A feature extraction method for biometric information detection, the feature extraction method comprising:
acquiring a bio-signal;
adjusting an asymmetry factor for component pulses of the No-signal;
decomposing a waveform of the acquired bio-signal into the component pulses based on adjusting the asymmetry factor; and
extracting a feature for the biometric information detection based on characteristic points of each of the component pulses.

13. The feature extraction method of claim 12, wherein the decomposing comprises obtaining a subsequent component pulse based on a new bio-signal generated based on one of the component pulses.

14. The feature extraction method of claim 13, wherein the decomposing comprises:
estimating a given component pulse to be decomposed, among the component pulses, based on the waveform of the bio-signal; and
generating the given component pulse based on the estimation result.

15. The feature extraction method of claim 14, further comprising, when the given component pulse is generated, eliminating the generated component pulse from the bio-signal,
wherein the estimating of the given component pulse comprises, when a number of generated component pulses is smaller than a pre-set number, estimating another subsequent component pulse based on another new bio-signal generated by eliminating the generated component pulse.

16. The feature extraction method of claim 14, wherein the estimating of the given component pulse comprises modeling a component pulse waveform function based on the waveform of the bio-signal and estimating parameters of the component pulse waveform function.

17. The feature extraction method of claim 16, wherein the modeling of the component pulse waveform function comprises modeling the component pulse waveform function to be bilaterally asymmetric with respect to a time axis, based on a Gaussian waveform function and the asymmetry factor.

18. The feature extraction method of claim 17, further comprising adjusting the asymmetry factor for a waveform of the given component pulse to be estimated.

19. The feature extraction method of claim 18, wherein the adjusting of the asymmetry factor comprises:
estimating the given component pulse based on the bio-signal and the asymmetry factor;
eliminating the estimated component pulse from the bio-signal;
comparing a mean time period of the bio-signal from which the component pulse is eliminated with a time period at a peak point, and,
in response to determining that the mean time period is smaller than the time period at a peak point, adjusting the asymmetry factor and re-estimating the given component pulse.

20. A biometric information detection apparatus comprising:
a sensor configured to emit light onto a user's skin, detect the light reflecting from the user's skin, and measure a bio-signal based on the detected light; and
a processor configured to adjust an asymmetry factor for component pulses of the bio-signal, decompose a waveform of the bio-signal into the component pulses based on adjusting the asymmetry factor, extract a feature of the bio-signal based on characteristic points of the component pulses, and detect biometric information based on the feature.

21. The biometric information detection apparatus of claim 20, wherein the processor is further configured to obtain a subsequent component pulse based on a new bio-signal generated based on one of the component pulses.

22. The biometric information detection apparatus of claim 21, wherein the processor is further configured to model a component pulse waveform function which is asymmetric with respect to a time axis, based on a Gaussian waveform function and the asymmetry factor, and decompose the bio-signal into the component pulses based on the modeled component pulse waveform function.

23. The biometric information detection apparatus of claim 20, wherein the processor is further configured to extract the feature based on characteristic points which include one or more of time, an amplitude, a standard deviation, and an offset of the component pulses.

24. The biometric information detection apparatus of claim 20, further comprising a communication interface configured to transmit the measured bio-signal to a feature extraction apparatus and receive, from the feature extraction apparatus, at least one of one or more additional component pulses decomposed based on the bio-signal, characteristic points of each of the additional component pulses, and a feature extracted based on the characteristic points.

25. The biometric information detection apparatus of claim 20, wherein the biometric information comprises one or more of blood pressure, a vascular age, a degree of arterial stiffness, an aortic pressure waveform, a stress index, and a degree of fatigue.

26. A wearable device comprising:
a main body;
a sensor provided in the main body and configured to emit light onto a user's skin, detect the light reflecting from the user's skin, and measure a bio-signal based on the detected light;
a processor provided in the main body and configured to acquire the bio-signal by controlling the sensor, adjust an asymmetry factor for component pulses of the bio-signal, decompose a waveform of the acquired bio-signal into the component pulses based on adjusting the asymmetry factor, extract a feature based on characteristic points of the component pulses, detect biometric information using the extracted feature, and generate a processing result based on the detected biometric information; and
a display provided in the main body and configured to display the processing result of the processor.

27. The wearable device of claim 26, wherein the display comprises a first section configured to display the detected biometric information or changes in the detected biometric information.

28. The wearable device of claim 27, wherein the display further comprises a second section configured to display component pulses used to detect biometric information which is selected from the first section.

29. The wearable device of claim 28, wherein the display is configured to display a mark in the first section for indicating the detected biometric information or the biometric information selected from the first section.

30. The wearable device of claim 26, further comprising a communication interface provided in the main body and configured to establish a connection with an external device for communication and transmit the processing result of the processor to the external device via the connection.

* * * * *